United States Patent
Barker

(10) Patent No.: US 10,255,770 B2
(45) Date of Patent: Apr. 9, 2019

(54) SYSTEM AND METHOD FOR NUTRIENT LEAKAGE DETECTION

(71) Applicant: Deere & Company, Moline, IL (US)

(72) Inventor: Mark E. Barker, Johnston, IA (US)

(73) Assignee: DEERE & COMPANY, Moline, IL (US)

( * ) Notice: Subject to any disclaimer, the term of this patent is extended or adjusted under 35 U.S.C. 154(b) by 0 days.

(21) Appl. No.: 15/596,962

(22) Filed: May 16, 2017

(65) Prior Publication Data

US 2018/0336767 A1  Nov. 22, 2018

(51) Int. Cl.
| | |
|---|---|
| G08B 5/36 | (2006.01) |
| G01N 25/00 | (2006.01) |
| G01N 33/24 | (2006.01) |
| G08B 3/10 | (2006.01) |

(52) U.S. Cl.
CPC ............. *G08B 5/36* (2013.01); *G01N 25/00* (2013.01); *G01N 33/24* (2013.01); *G08B 3/10* (2013.01); *G01N 2033/245* (2013.01)

(58) Field of Classification Search
CPC . G08B 5/36; G08B 3/10; G01N 25/00; G01N 33/24; A01G 25/16; A01G 27/00; G05D 7/0617; G05D 7/0676
See application file for complete search history.

(56) References Cited

U.S. PATENT DOCUMENTS

| | | |
|---|---|---|
| 5,967,066 A | 10/1999 | Giles et al. |
| 6,422,162 B1 | 7/2002 | Nimberger et al. |
| 9,532,499 B2 | 1/2017 | Anderson et al. |
| 2015/0373905 A1* | 12/2015 | Anderson ............. A01C 21/00 701/50 |
| 2016/0007524 A1 | 1/2016 | Kusler et al. |
| 2017/0031365 A1 | 2/2017 | Sugumaran et al. |

OTHER PUBLICATIONS

Researchgate, UAV-Based Gas Pipeline Leak Detection, Abstract: Asian Conference on Remote Sensing, Oct. 2014.
Journal of Geophysical Research: Atmospheres, Abstract: Open-path, near-infrared tunable diode laser spectrometer for atmospheric measurements of H2O, First published Aug. 1, 1998.
Engadget, NASA's Flying Methane Meter Built for Mars Finds Work on Earth, https://www.engadget.com/2016/03/28/nasa-s-flying-methane-meter-builtfor-mars-finds-work-on-earth/, Mar. 28, 2016.

* cited by examiner

*Primary Examiner* — Kabir A Timory
(74) *Attorney, Agent, or Firm* — Klintworth & Rozenblat IP LLP

(57) ABSTRACT

System and method for detecting a leakage of a nutrient from soil is provided. The nutrient is applied by a nutrient applicator associated with a work vehicle. The method includes receiving, by one or more processors, sensor signals from at least one sensor coupled to a nutrient applicator that observes a temperature of the soil and generates sensor signals based on the observation. The method includes determining, by the one or more processors, whether the observed temperature of the soil exceeds a pre-defined threshold temperature. The method includes generating, by the one or more processors, one or more notifications to a human-machine interface that the nutrient has leaked from the soil based on the observed temperature exceeding the pre-defined threshold temperature.

18 Claims, 5 Drawing Sheets

SYSTEM AND METHOD FOR NUTRIENT LEAKAGE DETECTION

CROSS-REFERENCE TO RELATED APPLICATION(S)

Not applicable.

STATEMENT OF FEDERALLY SPONSORED RESEARCH OR DEVELOPMENT

Not applicable.

FIELD OF THE DISCLOSURE

This disclosure relates to agricultural nutrient applicators and the detection of escaping gaseous nutrients deposited into the ground by a nutrient applicator.

BACKGROUND OF THE DISCLOSURE

Generally, in the agriculture industries, one or more nutrients may be added into the soil to improve crop yield and/or to restore a nutrient content of the soil after a harvest. In certain examples, anhydrous ammonia may be introduced into the soil to restore nitrogen levels within the soil. Typically, the anhydrous ammonia is introduced into the soil by an applicator mechanism. In one example, a sharp ground-engaging tool such as a shank or disk first cuts through the soil and creates a trench into which the anhydrous ammonia is subsequently deposited.

In certain instances, due to soil conditions, the position of the ground-engaging tool, environmental conditions, etc., the anhydrous ammonia may not be deposited completely into the soil. Generally, an operator of the work vehicle is not aware the anhydrous ammonia is not being deposited into the soil until a white cloud of water vapor is produced by the vaporization of the anhydrous ammonia in the air. Typically, the white cloud is visible for larger concentrations of anhydrous ammonia that have entered the air. In instances where smaller concentrations are not entering the soil, the operator may be unaware that the soil is not receiving the nutrient, which may result in a reduced crop yield.

SUMMARY OF THE DISCLOSURE

The disclosure provides a system and method for detecting that a nutrient, such as anhydrous ammonia, in various concentrations, has escaped or leaked into the air after being deposited into the ground by a nutrient applicator.

In one aspect the disclosure provides a method for detecting a leakage of a nutrient from soil. The nutrient is applied by a nutrient applicator associated with a work vehicle. The method includes receiving, by one or more processors, sensor signals from at least one sensor coupled to a nutrient applicator that observes a temperature of the soil and generates sensor signals based on the observation. The method includes determining, by the one or more processors, whether the observed temperature of the soil exceeds a pre-defined threshold temperature. The method includes generating, by the one or more processors, one or more notifications to a human-machine interface that the nutrient has leaked from the soil based on the observed temperature exceeding the pre-defined threshold temperature.

In another aspect the disclosure provides a system for detecting a leakage of a nutrient from soil. The nutrient is applied by a nutrient applicator associated with a work vehicle. The system includes at least one sensor coupled to a nutrient applicator that observes a temperature of the soil and generates sensor signals based on the observation. The system includes a controller, having one or more processors, that: process the sensor signals to determine a change in temperature of the soil; determine whether the change in temperature of the soil exceeds a pre-defined threshold for the change in temperature; and generate one or more notifications to an operator of the work vehicle that the nutrient has leaked from the soil based on the change in temperature of the soil exceeding the pre-defined threshold.

In yet another aspect the disclosure provides a system for detecting a leakage of a nutrient from soil. The nutrient is applied by a nutrient applicator associated with a work vehicle. The system includes at least one sensor coupled to a nutrient applicator that observes a temperature of the soil and generates sensor signals based on the observation. The at least one sensor is coupled to the nutrient applicator so as to be positioned behind the nutrient applicator in a direction of travel of the work vehicle. The system includes a controller, having one or more processors, that: receive the sensor signals from at least one sensor coupled to the nutrient applicator; process the sensor signals to determine an initial temperature of the soil; receive the sensor signals from at least one sensor and process the sensor signals to determine a current temperature of the soil; compare the initial temperature to the current temperature of the soil to determine a change in temperature of the soil; determine whether the change in temperature of the soil exceeds a pre-defined threshold for the change in temperature; and generate one or more notifications to an operator of the work vehicle that the nutrient has leaked from the soil based on the change in temperature of the soil exceeding the pre-defined threshold.

The details of one or more embodiments are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION

Figure 1:
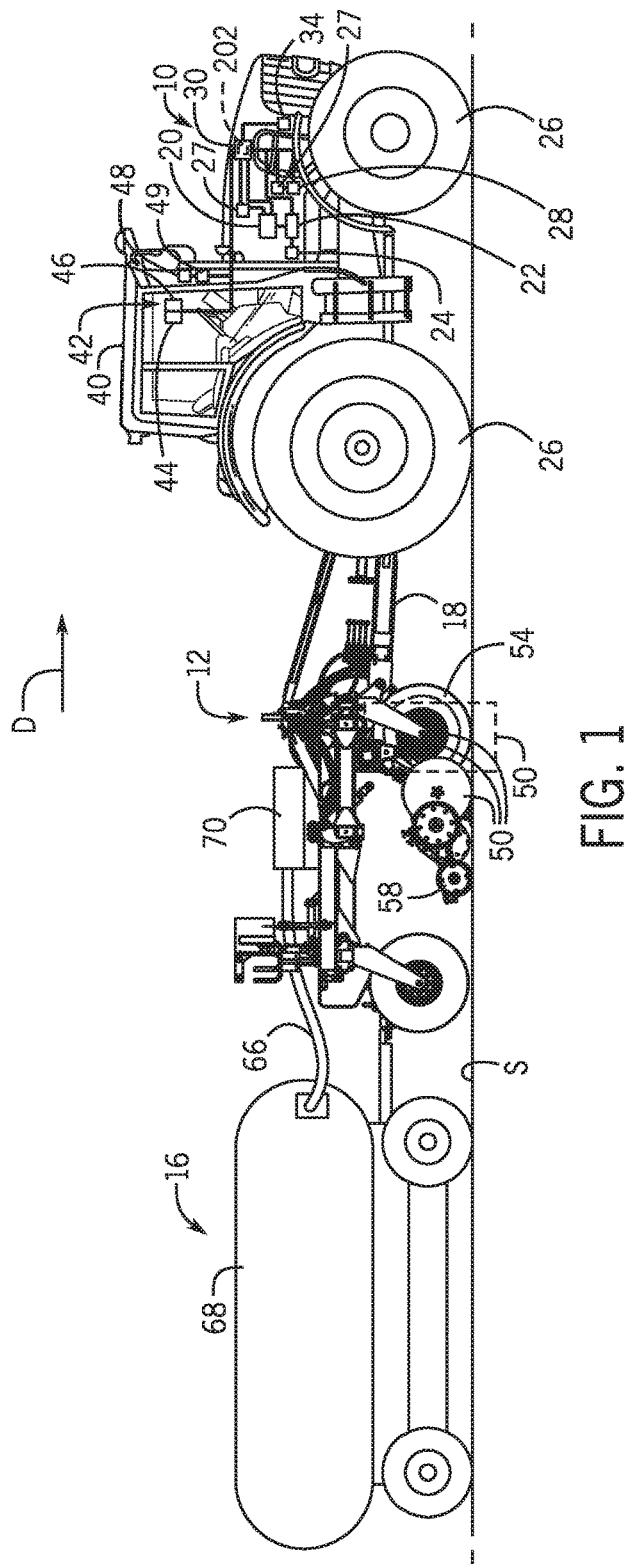
FIG. 1 is a side view of an example work vehicle in the form of an agricultural tractor towing a nutrient applicator in which the disclosed nutrient leakage detection system and method may be used.

The following describes one or more example embodiments of the disclosed system and method, as shown in the accompanying figures of the drawings described briefly above. Various modifications to the example embodiments may be contemplated by one of skill in the art.

As used herein, unless otherwise limited or modified, lists with elements that are separated by conjunctive terms (e.g., "and") and that are also preceded by the phrase "one or more of" or "at least one of" indicate configurations or arrangements that potentially include individual elements of the list, or any combination thereof. For example, "at least one of A, B, and C" or "one or more of A, B, and C" indicates the possibilities of only A, only B, only C, or any combination of two or more of A, B, and C (e.g., A and B; B and C; A and C; or A, B, and C).

As used herein, the term module refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

Embodiments of the present disclosure may be described herein in terms of functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present disclosure may be practiced in conjunction with any number of systems, and that the work vehicle described herein is merely one example embodiment of the present disclosure.

For the sake of brevity, conventional techniques related to signal processing, data transmission, signaling, control, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the present disclosure.

Discussion herein may sometimes focus on the example application of a nutrient applicator coupled to a work vehicle, which receives a nutrient, such as anhydrous ammonia, from a nutrient tank. In other applications, other configurations are also possible. In some embodiments, for example, the nutrient tank may be coupled to the work vehicle.

The following describes one or more example implementations of the disclosed system for nutrient leakage detection, as shown in the accompanying figures of the drawings described briefly above. Generally, the disclosed systems (and work vehicles in which they are implemented) provide for improved notification to the operator that the nutrient is leaking from the soil. In this regard, the disclosed system detects a leakage of the nutrient before the nutrient has leaked to the extent it is visible by the operator, which enables the operator to adjust the nutrient applicator (e.g. change closing wheel settings), adjust the nutrient applicator (e.g. increase operating depth), and/or determine whether to proceed with the application of the nutrient (e.g. cease to operate). The notification of a leakage before it is visible to the operator also ensures that the soil receives the proper amount of the nutrient.

In the following, the nutrient applied is anhydrous ammonia, and it is usually directly injected as a crystal, liquid, or semi-liquid into the ground or soil before or after planting. Although soil is placed over the anhydrous ammonia to prevent it from escaping, in certain instances, due to the closing depth of one or more soil closing tools, some of the liquid or semi-liquid may escape. As anhydrous ammonia boils at negative 26 degrees Fahrenheit, the escaped anhydrous ammonia causes a temperature drop at the soil. The disclosed nutrient leakage detection system measures the temperature of the soil or ground, and determines whether a temperature drop has been observed. If a temperature change or drop has been observed that is greater than or exceeds a threshold for a change in temperature, such as a change in temperature greater than about negative 10 degrees Fahrenheit to about negative 20 degrees Fahrenheit, the disclosed nutrient leakage detection system outputs one or more notifications to the operator to notify the operator of the detected leakage. For example, the disclosed nutrient leakage detection system may output one or more control signals to illuminate an indicator light, one or more control signals to announce an audible message and/or operator interface data for rendering a graphical and/or textual message on a display within the tractor that notifies the operator of the leakage. Based on the one or more notifications, the operator may adjust the nutrient applicator (e.g. change closing wheel settings), adjust the nutrient applicator (e.g. increase operating depth) and/or determine whether to proceed with the application of the nutrient (e.g. cease to operate).

In one example, the disclosed nutrient leakage detection system includes a sensor, such as a thermocouple, mounted on a sensor mounting bracket that is coupled to the nutrient applicator. The sensor mounting bracket positions the sensor a distance above the soil or ground, for observing the temperature of the soil or ground. By mounting the sensor close to the soil or ground, the sensor is less influenced by environmental conditions. In one example, the nutrient applicator includes three sensor mounting brackets and three sensors, with a respective sensor mounting bracket and sensor for each of a main frame, a first wing and a second wing, thereby defining three monitoring zones. It should be understood, however, that the nutrient applicator may include any number of monitoring zones that are monitored by a respective sensor coupled to a sensor mounting bracket, and the following description is merely an example. Each of the sensor mounting brackets is coupled to the nutrient applicator so as to be disposed behind the nutrient applicator in a direction of travel of the tractor.

As noted above, the disclosed nutrient leakage detection system may be utilized with regard to various machines or work vehicles with nutrient applicators, including tractors and other work vehicles. Referring to FIG. 1, in some embodiments, a nutrient leakage detection system 100 may be used with a tractor 10 coupled to a nutrient applicator 12 for detecting a leakage of a nutrient applied by the nutrient applicator 12 into soil S, such as anhydrous ammonia provided in a nutrient tank 16. It should be noted that while the following discussion refers to the nutrient as anhydrous ammonia, the teachings of the present disclosure may be applicable to other nutrients and/or pesticides.

Generally, the tractor 10 is coupled to the nutrient applicator 12 via a draw bar 18 or other coupling device. The tractor 10 includes a source of propulsion, such as an engine 20. The engine 20 supplies power to a transmission 22. The transmission 22 transfers the power from the engine 20 to a suitable driveline 24 coupled to one or more drive wheels 26 of the tractor 10 to enable the tractor 10 to move. In one example, the engine 20 is an internal combustion engine, such as a diesel engine. It should be noted that the use of an internal combustion engine is merely exemplary, as the propulsion device can be a fuel cell, electric motor, a hybrid-electric motor, etc.

The tractor 10 also includes one or more pumps 27, which may be driven by the engine 20 of the tractor 10. Flow from the pumps 27 may be routed through various control valves 28 and various conduits (e.g., flexible hoses and lines) to control various components associated with the tractor 10. Flow from the pumps 27 may also power various other components of the tractor 10. The flow from the pumps 27 may be controlled in various ways (e.g., through control of the various control valves 28 and/or a controller 30 associated with the tractor 10).

Generally, the controller 30 (or multiple controllers) may be provided, for control of various aspects of the operation of the tractor 10, in general. The controller 30 (or others) may be configured as a computing device with associated processor devices and memory architectures, as a hard-wired computing circuit (or circuits), as a programmable circuit, as a hydraulic, electrical or electro-hydraulic controller, or otherwise. As such, the controller 30 may be configured to execute various computational and control functionality with respect to the tractor 10 (or other machinery). In some embodiments, the controller 30 may be configured to receive input signals in various formats (e.g., as hydraulic signals, voltage signals, current signals, and so on), and to output command signals in various formats (e.g., as hydraulic signals, voltage signals, current signals, mechanical movements, and so on). In some embodiments, the controller 30 (or a portion thereof) may be configured as an assembly of hydraulic components (e.g., valves, flow lines, pistons and cylinders, and so on), such that control of various devices (e.g., pumps or motors) may be effected with, and based upon, hydraulic, mechanical, or other signals and movements.

The controller 30 may be in electronic, hydraulic, mechanical, or other communication with various other systems or devices of the tractor 10 (or other machinery, such as the nutrient applicator 12 coupled to the tractor 10). For example, the controller 30 may be in electronic or hydraulic communication with various actuators, sensors, and other devices within (or outside of) the tractor 10, including various devices associated with the pumps 27, control valves 28, and so on. The controller 30 may communicate with other systems or devices (including other controllers, such as a controller associated with the nutrient applicator 12) in various known ways, including via a CAN bus (not shown) of the tractor 10, via wireless or hydraulic communication means, or otherwise. The controller 30 is in communication with one or more sensors 104 of the nutrient leakage detection system 100 over a communication medium that facilitates the transfer of power, data, commands, etc., such as a CAN bus. As will be discussed, the controller 30 receives and processes sensor signals received from the sensors 104 of the nutrient leakage detection system 100 and generates one or more notifications based on the processing.

Various sensors may also be provided to observe various conditions associated with the tractor 10. In some embodiments, various sensors 34 (e.g., pressure, flow or other sensors) may be disposed near the pumps 27 and control valves 28, or elsewhere on the tractor 10. For example, sensors 34 observe a pressure associated with the pumps 27 and generate sensor signals based thereon.

The tractor 10 also includes a cab 40, which includes a human-machine interface 42. The controller 30 receives input commands and interfaces with the operator via the human-machine interface 42. The human-machine interface 42 may be configured in a variety of ways. In some embodiments, the human-machine interface 42 may include one or more joysticks, various switches or levers, one or more buttons, a touchscreen interface 44 that may be overlaid on a display 46, a keyboard, an audible device, such as a speaker 48, one or more indicator lights 49, a microphone associated with a speech recognition system, or various other human-machine interface devices. The human-machine interface 42 is in communication with the controller 30 over a communication medium that facilitates the transfer of power, data, commands, etc., such as a CAN bus.

The display 46 comprises any suitable technology for displaying information, including, but not limited to, a liquid crystal display (LCD), organic light emitting diode (OLED), plasma, or a cathode ray tube (CRT). In this example, the display 46 is an electronic display capable of graphically displaying one or more operator interfaces under the control of the controller 30. Those skilled in the art may realize other techniques to implement the display 46 in the tractor 10. The speaker 48 is responsive to one or more control signals from the controller 30 to output an audible message, such as "Warning—Leak Detected First Zone" or similar.

The indicator lights 49 may be disposed in an instrument panel associated with the tractor 10, or may be disposed at any location that is visible by an occupant of the tractor 10. The indicator lights 49 are each responsive to one or more control signals from the controller 30 to illuminate, thereby notifying the operator of a leakage of the nutrient. In one example, the indicator lights 49 are each a light emitting diode (LED), however, the indicator light 49 may comprise any illumination device or source responsive to one or more control signals from the controller 30, including, but not limited to, an organic light emitting diode (OLED), etc. The indicator lights 49 may also be disposed behind one or more words or symbols, to illuminate the one or more words or symbols to visually indicate to the operator the leakage of the nutrient. In this example, the indicator light 49 may illuminate a symbol of an engine and/or may illuminate text that reads "Leak Detected." In one example, an indicator light 49 may be associated with a respective one of the nutrient leakage detection system 100 so that the operator may be informed as to which particular monitoring zone has a detected leakage of the nutrient.

The nutrient applicator 12 includes soil opening tools 50 such as coulters, disks or shanks that disturb and cut into the ground and create openings such as holes, slivers, slices, furrows or trenches in the soil. The nutrient applicator 12 includes fingers or nutrient tubes 54 that direct nutrients into the soil. Although called a "tube," the nutrient tubes 54 are alternatively tubular, conical, funnel-shaped, syringe or some other dispenser shape that can accurately place nutrients in a small area (e.g. within 1-2 inches of a desired location). Each of the nutrient tubes 54 has a tube opening 56 where nutrients are dispensed into the soil S (see e.g. FIG. 4). The nutrient applicator 12 also includes one or more soil closing tools 58, such as closing disks, which are positioned behind the nutrient tubes 54 in the direction of travel D of the tractor 10. As will be discussed, in this example, a portion of the nutrient leakage detection system 100 is positioned a distance behind one or more of the soil closing tools 58 in the direction of travel D of the tractor 10.

Also depending on the size and span-width of the tractor 10, more than one nutrient applicator 12 may be attached to the rear of the tractor 10, either in the lateral direction (e.g. perpendicular to direction of travel) or in series such as when there are multiple types of nutrients that are not mixed together. In one example, with reference to FIG. 2, the nutrient applicator 12 includes a main frame 60 and a pair of wings 62 (i.e. a first, left wing 62' and a second, right wing 62"). Each of the wings 62', 62" may be movably coupled to the main frame 60 such that the wings 62', 62" may be pivoted upward, for example, to aid the tractor 10 in pulling the nutrient applicator 12 on a roadway, for example. As will be discussed, in this example, a portion of the nutrient leakage detection system 100 is coupled to each of the main frame 60, the left wing 62' and the right wing 62". The portion of the nutrient leakage detection system 100 coupled to the main frame 60 may be considered to define a first monitoring zone, the portion of the nutrient leakage detection system 100 coupled to the left wing 62' may be considered to define a second monitoring zone; and the portion of the nutrient leakage detection system 100 coupled to the right wing 62" may be considered to define a third monitoring zone.

Figure 2:
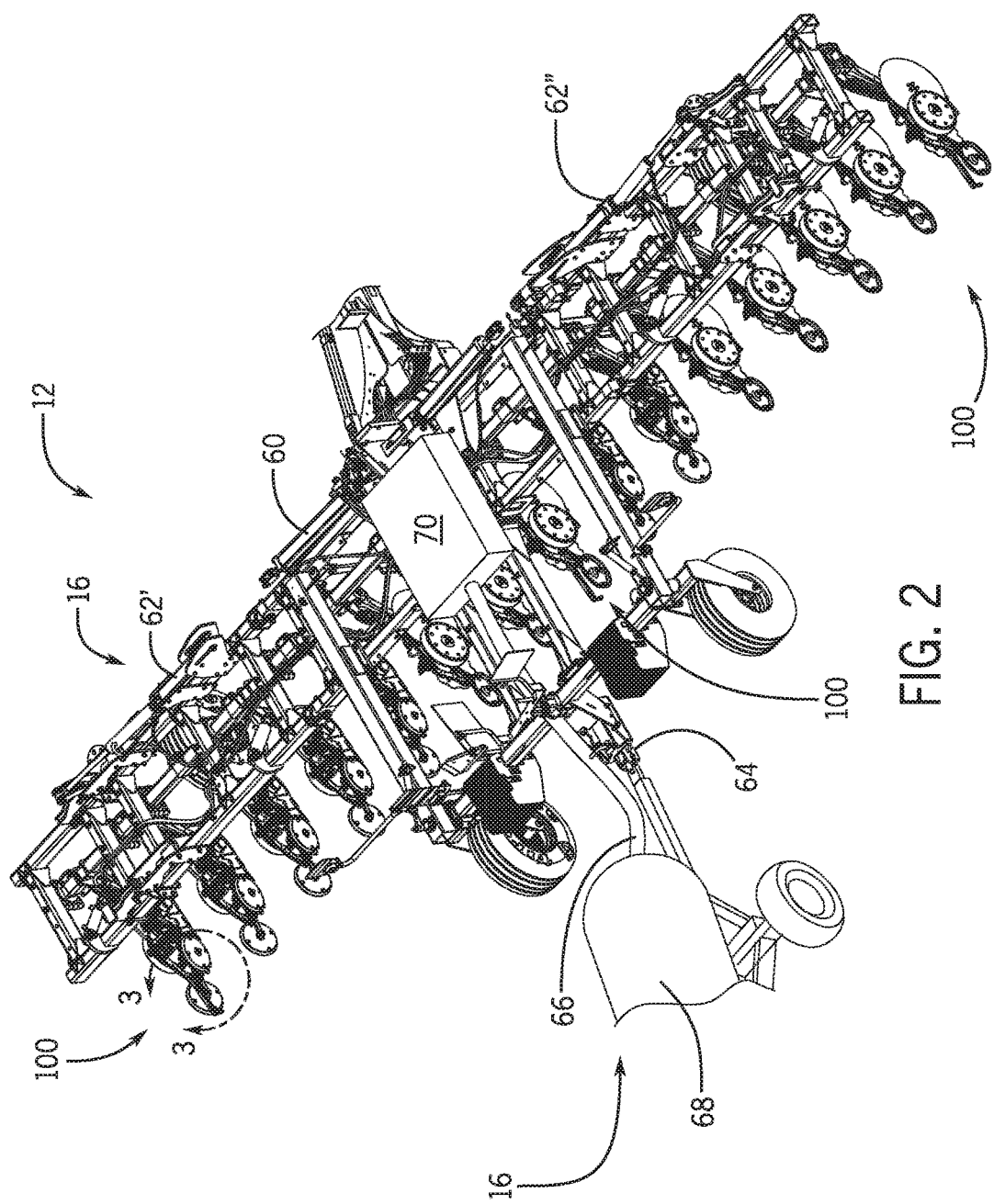
FIG. 2 is a partial perspective view of a nutrient applicator, which includes the nutrient leakage detection system of FIG. 1.

With continued reference to FIG. 2, the nutrient applicator 12 has a rear hitch 64, to which heavy loads may be attached and pulled, such as the nutrient tank 16. The nutrient tank 16 supplies or feeds nutrients into the nutrient applicator 12 via a feed duct 66. For instance, the nutrient tank 16 is a liquid anhydrous ammonia ($NH_3$) tank 68. Alternatively, tank 68 is mounted on the tractor 10. Generally, a manifold 70 is mounted on the nutrient applicator 12 that directs or re-directs compounds from the tank 68 to the appropriate corresponding nutrient tubes 54. In this example, the anhydrous ammonia flows from the tank 68 through the feed duct 66 and into the manifold 70 before being distributed through various ducts and tubings into the respective nutrient tubes 54 and then into the soil.

Figure 3:
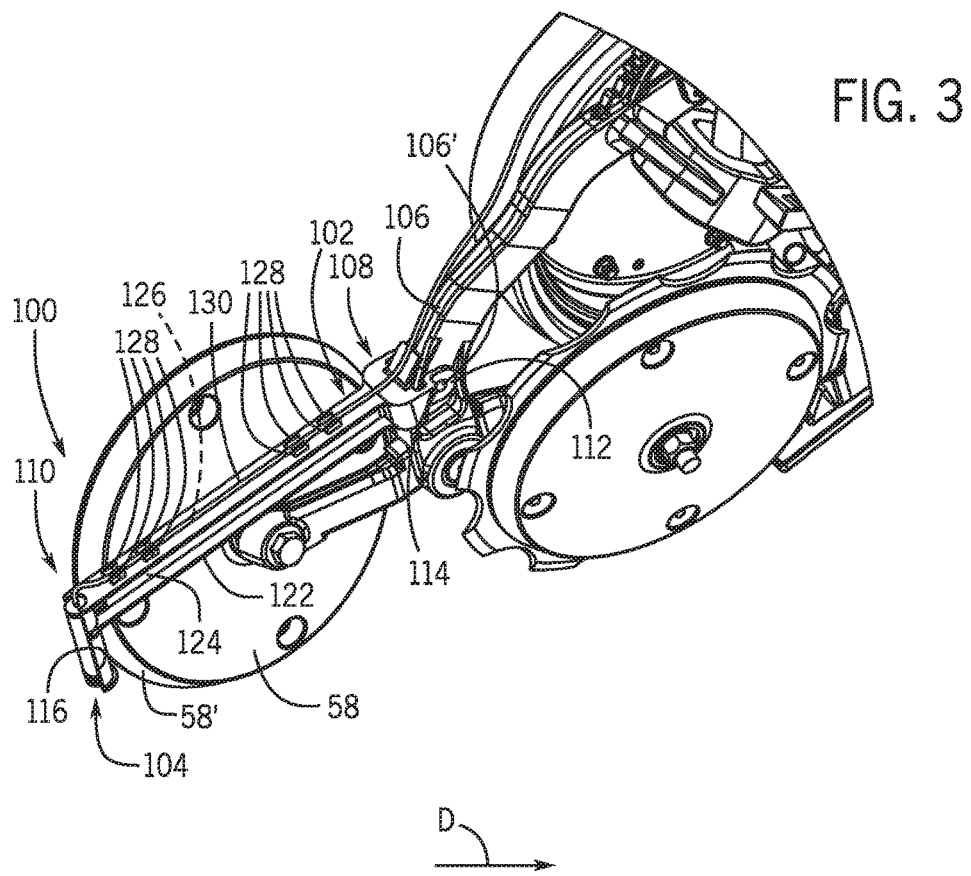
FIG. 3 is a partial perspective view taken at 3-3 of FIG. 2, which illustrates the nutrient leakage detection system coupled to one row unit of the nutrient applicator.

With reference to FIG. 3, a portion of the nutrient leakage detection system 100 is shown in greater detail. In this example, the nutrient leakage detection system 100 includes a sensor mounting bracket 102 and a sensing device or sensor 104. In this example, each of the main frame 60, left wing 62' and the right wing 62" include a respective one of the sensor mounting bracket 102 and the sensor 104.

Figure 4:
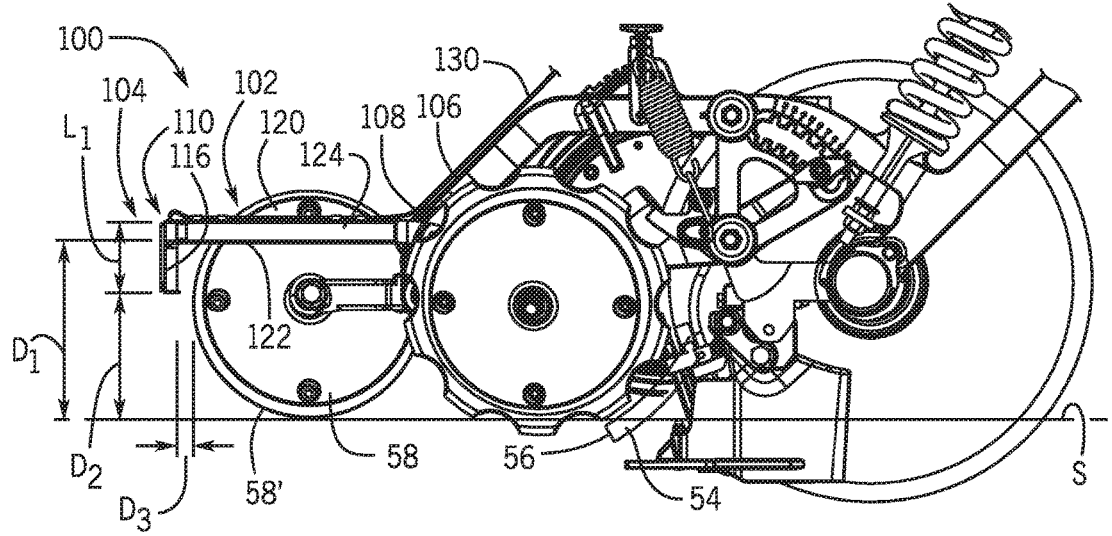
FIG. 4 is a partial side view thereof.

With brief reference to FIG. 4, the sensor mounting bracket 102 is coupled to a portion of the nutrient applicator 12, and in one example, is coupled to a mount 106 of one of the soil closing tools 58 so as to be disposed a distance D1 above the soil S. In this example, the sensor mounting bracket 102 is coupled to the mount 106 so as to extend along an axis substantially parallel to the surface of the soil S. By positioning the sensor mounting bracket 102 substantially parallel to the soil S, the sensor mounting bracket 102 aligns the sensor 104 coupled to the sensor mounting bracket 102 toward the soil S adjacent to an outer circumference 58' of the one of the soil closing tools 58. In this example, the sensor 104 is coupled to the sensor mounting bracket 102 so as to be substantially perpendicular to the soil S. The sensor mounting bracket 102 may be composed of a metal, metal alloy or a polymer, and may be cast, machined, stamped, molded, printed, etc.

In one example, the sensor mounting bracket 102 includes a first end 108 and an opposite second end 110. With reference to FIG. 3, the first end 108 has a pair of arms 112 that define a substantially U-shape for positioning on opposed sides 106' of the mount 106. In one example, each of the arms 112 defines a bore 114, which is coaxially aligned with a bore 106" defined through the mount 106 to receive a mechanical fastener, such as a bolt and nut, etc. to couple the sensor mounting bracket 102 to the mount 106. It should be understood, however, that a variety of different techniques may be employed to couple the sensor mounting bracket 102 to the mount 106, including a hook and loop fastener, C-clamp, cable, cotter pin, etc. Alternatively, the sensor mounting bracket 102 may also be welded or secured to the mount 106 via adhesives.

The second end 110 defines a recess 116 that is substantially C-shaped for receiving a portion of the sensor 104. With reference to FIG. 4, the second end 110 extends for a length L1, which is sized such that the second end 110 supports the sensor 104 substantially over a length of the sensor 104. It should be noted that the second end 110 may have any desired length, and need not correspond substantially with the length of the sensor 104. Generally, the recess 116 is sized such that the sensor 104 may be press or snap fit into the recess 116 to releasably retain the sensor 104; however, the second end 110 may include a hook and loop fastener strap, a cotter pin, or other devices that may be used to releasably retain the sensor 104 within the recess 116.

The sensor mounting bracket 102 also includes a first surface 120 opposite a second surface 122, and a first side 124 opposite a second side 126. The first surface 120 is generally opposite the soil S, and includes one or more guides 128. Generally, the first surface 120 includes pairs of guides 128 spaced apart along a width of the first surface 120, with two of the pairs of guides 128 spaced apart along a length of the first surface 120 to guide a wire or cable 130 associated with the sensor 104 along the sensor mounting bracket 102. The second surface 122 generally faces the soil S. The first side 124 and the second side 126 may be recessed relative to the first surface 120 and the second surface 122 to provide a mass savings.

The sensor 104 is coupled to the second end 110 of the sensor mounting bracket 102. Generally, the sensor 104 is coupled to the second end 110 so as to be a distance D2 from the ground or soil S. In one example, D2 is about 3 inches to about 12 inches. The sensor 104 is generally positioned a distance D3 behind the outer circumference 58' of the soil closing tool 58 in the direction of travel D of the tractor 10 (FIG. 1). Distance D3 is generally less than D1 and D2, and is generally selected to ensure that the sensor 104 observes soil S that is settled or has been closed by the soil closing tool 58. The sensor 104 observes a condition of the ground, which includes the soil S, adjacent to the soil closing tool 58 and generates sensor signals based thereon. In one example, the sensor 104 is a thermocouple, and observes a temperature of the soil S. As used herein, the "temperature of the soil S" includes a temperature of a surface of the soil S or ground, and may include a reflected surface temperature of the soil S or ground. In this example, the sensor 104 is an infrared thermocouple, which has a sensing diameter of about 1.0 inch (in.). Generally, the sensor 104 is capable of observing an ambient temperature from about 0 degrees Fahrenheit to about 80 degrees Fahrenheit. It should be noted that the sensor 104 need not comprise an infrared thermocouple, but rather any sensing device capable of observing an ambient temperature of a ground surface or of a boundary layer of air above a ground surface, including the soil S, may be employed with the nutrient leakage detection system 100. In this example, the sensor 104 is coupled to the sensor mounting bracket 102 such that the infrared beam emitted by the sensor 104 is directed at a trench that has been closed by the soil closing tool 58 after the nutrient has been inserted into the trench. The sensor mounting bracket 102 maintains the sensor 104 substantially perpendicular to the surface of the soil or ground.

The various components noted above (or others) may be utilized by the controller 30 to detect a leakage of the nutrient, and to notify an operator of the leakage of the nutrient via the human-machine interface 42. Accordingly, these components may be viewed as forming part of the nutrient leakage detection system 100 for the tractor 10. Each of the sensors 104 are in communication with the controller 30 via a suitable communication architecture, such as a CAN bus. The sensors 104 are illustrated herein as coupled to the controller 30 via cables 130, however, it should be understood that the sensors 104 may communicate with the controller 30 via a wireless communication architecture, if desired.

In various embodiments, the controller 30 receives and processes the sensor signals from each of the sensors 104 and determines whether the nutrient is leaking from the soil S. Based on the determination of a leak, the controller 30 outputs one or more notifications to the operator via the human-machine interface 42. For example, the controller 30 outputs one or more control signals to the speaker 48, outputs one or more control signals to one or more of the indicator lights 49 and outputs operator interface data for rendering on the display 46 that indicates a leak is detected in a particular monitoring zone.

Figure 5:
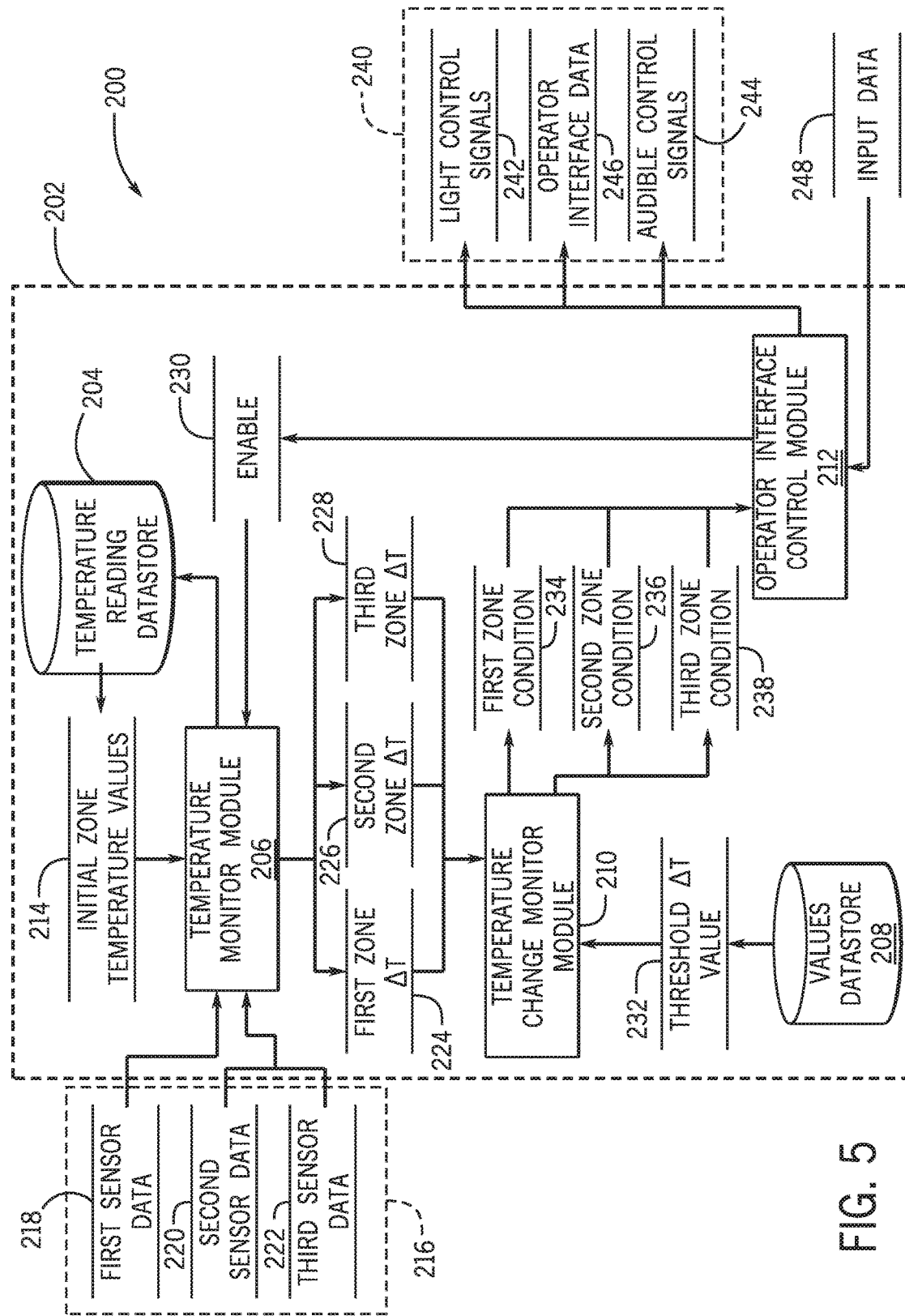
FIG. 5 is a dataflow diagram illustrating an example notification system of the nutrient leakage detection system of FIG. 1 in accordance with various embodiments.

Referring now also to FIG. 5, a dataflow diagram illustrates various embodiments of a notification system 200 of the nutrient leakage detection system 100 for the tractor 10, which may be embedded within a control module 202 associated with the controller 30. Various embodiments of the notification system 200 according to the present disclosure can include any number of sub-modules embedded within the control module 202. As can be appreciated, the sub-modules shown in FIG. 5 can be combined and/or further partitioned to similarly output one or more notifications to the human-machine interface 42. Inputs to the notification system 200 are received from the sensors 104 (FIG. 1), received from the human-machine interface 42 (FIG. 1), received from other control modules (not shown) associated with the tractor 10, and/or determined/modeled by other sub-modules (not shown) within the controller 30. In various embodiments, the control module 202 includes a temperature reading datastore 204, a temperature monitor module 206, a values datastore 208, a temperature change monitor module 210 and an operator interface control module 212.

The temperature reading datastore 204 stores initial zone temperature values 214 as observed by the sensors 104. The initial zone temperature values 214 stored in the temperature reading datastore 204 are populated by the temperature monitor module 206 based on an enabling of the notification system 200. Generally, the temperature reading datastore 204 stores an initial temperature for each of the monitoring zones, and thus, stores a temperature observed by the sensor 104 for the first monitoring zone (main frame 60), a temperature observed by the sensor 104 for the second monitoring zone (left wing 62') and a temperature observed by the sensor 104 for the third monitoring zone (right wing 62").

The temperature monitor module 206 receives as input sensor data 216. The sensor data 216 is the sensor signals or sensor data from each of the sensors 104 coupled to the tractor 10. Thus, in this example, the temperature monitor module 206 receives as input first sensor data 218, second sensor data 220 and third sensor data 222. The first sensor data 218 is the sensor signals or sensor data from the sensor 104 coupled to the first monitoring zone. The second sensor data 220 is the sensor signals or sensor data from the sensor 104 coupled to the second monitoring zone. The third sensor data 222 is the sensor signals or sensor data from the sensor 104 coupled to the third monitoring zone.

The temperature monitor module 206 processes the first sensor data 218 and determines a current temperature of the first monitoring zone. The temperature monitor module 206 queries the temperature reading datastore 204 and retrieves the initial zone temperature value 214 for the first monitoring zone. The temperature monitor module 206 compares the current temperature of the first monitoring zone to the initial zone temperature value 214 for the first monitoring zone and computes a first zone change in temperature 224. In one example, the temperature monitor module 206 subtracts the initial zone temperature value 214 for the first monitoring zone from the current temperature of the first monitoring zone to determine the first zone change in temperature 224. The temperature monitor module 206 sets the first zone change in temperature 224 for the temperature change monitor module 210.

The temperature monitor module 206 processes the second sensor data 220 and determines a current temperature of the second monitoring zone. The temperature monitor module 206 queries the temperature reading datastore 204 and retrieves the initial zone temperature value 214 for the second monitoring zone. The temperature monitor module 206 compares the current temperature of the second monitoring zone to the initial zone temperature value 214 for the second monitoring zone and computes a second zone change in temperature 226. In one example, the temperature monitor module 206 subtracts the initial zone temperature value 214 for the second monitoring zone from the current temperature of the second monitoring zone to determine the second zone change in temperature 226. The temperature monitor module 206 sets the second zone change in temperature 226 for the temperature change monitor module 210.

The temperature monitor module 206 processes the third sensor data 222 and determines a current temperature of the third monitoring zone. The temperature monitor module 206 queries the temperature reading datastore 204 and retrieves the initial zone temperature value 214 for the third monitoring zone. The temperature monitor module 206 compares the current temperature of the third monitoring zone to the initial zone temperature value 214 for the third monitoring zone and computes a third zone change in temperature 228. In one example, the temperature monitor module 206 subtracts the initial zone temperature value 214 for the third monitoring zone from the current temperature of the third monitoring zone to determine the third zone change in temperature 228. The temperature monitor module 206 sets the third zone change in temperature 228 for the temperature change monitor module 210.

The temperature monitor module 206 also receives as input enable 230. The enable 230 is received from the operator interface control module 212. Based on the enable 230, the temperature monitor module 206 receives and processes the sensor data 216 (i.e. the first sensor data 218, the second sensor data 220 and the third sensor data 222) to determine the temperature of each of the first monitoring zone, the second monitoring zone and the third monitoring zone. The temperature monitor module 206 stores the temperatures determined for each of the first monitoring zone, the second monitoring zone and the third monitoring zone in the temperature reading datastore 204 as the initial zone temperature values 214.

The values datastore 208 stores a threshold temperature change value 232. The threshold temperature change value 232 is a pre-defined, default value for a change in temperature, which may be factory set. In one example, the threshold temperature change value 232 is a value selected from a range of about negative 10 degrees Fahrenheit to about negative 20 degrees Fahrenheit. In one example, the threshold temperature change value 232 is about negative 20 degrees Fahrenheit.

The temperature change monitor module 210 receives as input the first zone change in temperature 224. Based on the first zone change in temperature 224, the temperature change monitor module 210 queries the values datastore 208 and retrieves the threshold temperature change value 232. The temperature change monitor module 210 compares the first zone change in temperature 224 to the threshold temperature change value 232. The temperature change monitor module 210 determines, based on the comparison, if the first zone change in temperature 224 is greater than or exceeds the threshold temperature change value 232. If true, the temperature change monitor module 210 sets first zone condition 234 for the operator interface control module 212. The first zone condition 234 indicates that a leakage has been detected in the first monitoring zone (main frame 60).

The temperature change monitor module 210 receives as input second zone change in temperature 226. Based on the second zone change in temperature 226, the temperature change monitor module 210 queries the values datastore 208 and retrieves the threshold temperature change value 232. The temperature change monitor module 210 compares the second zone change in temperature 226 to the threshold temperature change value 232. The temperature change monitor module 210 determines, based on the comparison, if the second zone change in temperature 226 is greater than or exceeds the threshold temperature change value 232. If true, the temperature change monitor module 210 sets second zone condition 236 for the operator interface control module 212. The second zone condition 236 indicates that a leakage has been detected in the second monitoring zone (left wing 62').

The temperature change monitor module 210 receives as input third zone change in temperature 228. Based on the third zone change in temperature 228, the temperature change monitor module 210 queries the values datastore 208 and retrieves the threshold temperature change value 232. The temperature change monitor module 210 compares the third zone change in temperature 228 to the threshold temperature change value 232. The temperature change monitor module 210 determines, based on the comparison, if the third zone change in temperature 228 is greater than or exceeds the threshold temperature change value 232. If true, the temperature change monitor module 210 sets third zone condition 238 for the operator interface control module 212. The third zone condition 238 indicates that a leakage has been detected in the third monitoring zone (right wing 62").

The operator interface control module 212 receives as input the first zone condition 234, the second zone condition 236 and the third zone condition 238. Based on receiving the first zone condition 234, the operator interface control module 212 outputs one or more notifications 240 to the human-machine interface 42 to notify the operator of the leakage detected in the first monitoring zone. In one example, the notifications 240 include one or more light control signals 242, one or more audible control signals 244 and operator interface data 246. The one or more light control signals 242 command the indicator light 49 associated with the first monitoring zone to illuminate, thereby notifying the operator of the leak. The one or more audible control signals 244 command the speaker 48 to output an audible message, such as "Warning—Leak Detected First Zone" and/or an audible tone. The operator interface data 246 includes data for rendering one or more graphical and/or textual messages on the display 46 that indicate that a leak has been detected in the first monitoring zone. For example, the operator interface data 246 may include instructions for rendering "Warning—Leak Detected First Zone" on the display 46 and/or may include instructions for rendering a graphical symbol of the nutrient applicator 12 with the first monitoring zone displayed in a different color, such as red, to graphically indicate the detected leak.

Based on receiving the second zone condition 236, the operator interface control module 212 outputs the one or more notifications 240 to the human-machine interface 42 to notify the operator of the leakage detected in the second monitoring zone. The one or more light control signals 242 command the indicator light 49 associated with the second monitoring zone to illuminate, thereby notifying the operator of the leak. The one or more audible control signals 244 command the speaker 48 to output an audible message, such as "Warning—Leak Detected Second Zone" and/or an audible tone. The operator interface data 246 includes data for rendering one or more graphical and/or textual messages on the display 46 that indicate that a leak has been detected in the second monitoring zone. For example, the operator interface data 246 may include instructions for rendering "Warning—Leak Detected Second Zone" on the display 46 and/or may include instructions for rendering a graphical symbol of the nutrient applicator 12 with the second monitoring zone displayed in a different color, such as red, to graphically indicate the detected leak.

Based on receiving the third zone condition 238, the operator interface control module 212 outputs the one or more notifications 240 to the human-machine interface 42 to notify the operator of the leakage detected in the third monitoring zone. The one or more light control signals 242 command the indicator light 49 associated with the third monitoring zone to illuminate, thereby notifying the operator of the leak. The one or more audible control signals 244 command the speaker 48 to output an audible message, such as "Warning—Leak Detected Third Zone" and/or an audible tone. The operator interface data 246 includes data for rendering one or more graphical and/or textual messages on the display 46 that indicate that a leak has been detected in the third monitoring zone. For example, the operator interface data 246 may include instructions for rendering "Warning—Leak Detected Third Zone" on the display 46 and/or may include instructions for rendering a graphical symbol of the nutrient applicator 12 with the third monitoring zone displayed in a different color, such as red, to graphically indicate the detected leak.

It should be noted that while the operator interface control module 212 is described herein as outputting the one or more notifications 240 for a particular zone, the operator interface control module 212 may also upon receipt of any one of the first zone condition 234, the second zone condition 236 and the third zone condition 238 output the one or more notifications 240 that are not zone specific.

The operator interface control module 212 also receives input data 248. The input data 248 is received based on the operator's interaction with the human-machine interface 42. For example, the operator may select a start button on the touchscreen interface 44 to initiate the start of the notification system 200. The operator interface control module 212 interprets the input data 248 and sets the enable 230 based on the input to the start button on the touchscreen interface 44, for example.

Figure 6:
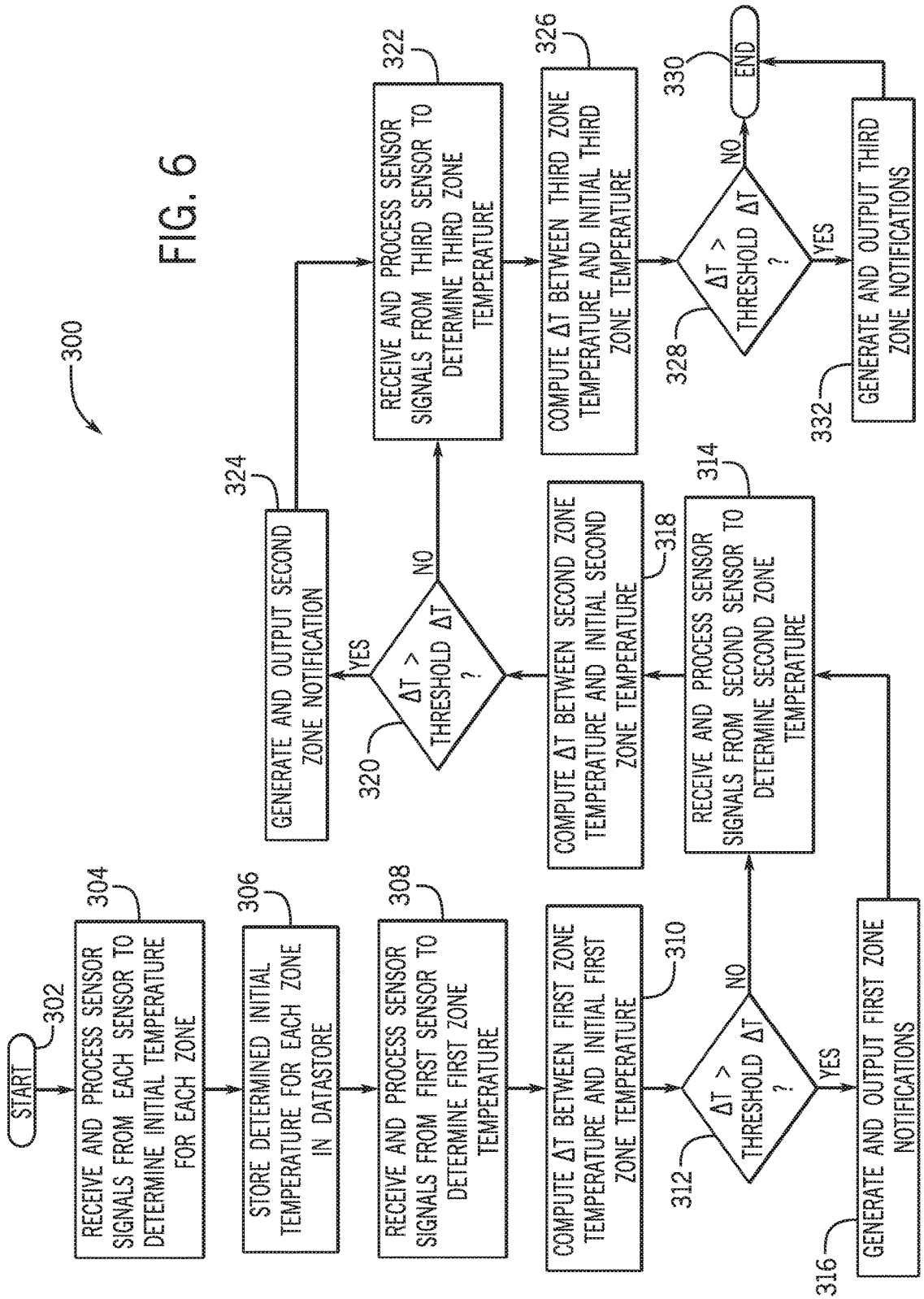
FIG. 6 is a flowchart illustrating an example method of the notification system of the nutrient leakage detection system of FIG. 1 in accordance with various embodiments.

Referring now also to FIG. 6, a flowchart illustrates a method 300 that may be performed by the control module 202 of the controller 30 of FIGS. 1 and 5 in accordance with the present disclosure. As can be appreciated in light of the disclosure, the order of operation within the method is not limited to the sequential execution as illustrated in FIG. 6, but may be performed in one or more varying orders as applicable and in accordance with the present disclosure. In various embodiments, the method 300 may be scheduled to run based on predetermined events, and/or can run continuously during operation of the tractor 10. Generally, the method 300 is initiated based on the receipt of the input data 248.

In one example, the method begins at 302. At 304, the method receives and processes the sensor data 216 (i.e. the first sensor data 218, the second sensor data 220 and the third sensor data 222) received from the sensors 104 to determine the initial temperature of each zone. At 306, the method stores the initial zone temperature values 214 in the temperature reading datastore 204. At 308, the method receives and processes the sensor signals from the sensor 104 of the first monitoring zone to determine the current temperature of the first monitoring zone. At 310, the method retrieves the initial zone temperature value 214 for the first monitoring zone and compares the initial zone temperature value 214 for the first monitoring zone to the current temperature of the first monitoring zone. The method determines or computes the first zone change in temperature 224, in one example, by subtracting the initial zone temperature value 214 for the first monitoring zone from the current temperature of the first monitoring zone to determine the first zone change in temperature 224.

At 312, the method retrieves the threshold temperature change value 232 from the values datastore 208 and compares the first zone change in temperature 224 to the threshold temperature change value 232. If the first zone change in temperature 224 is less than the threshold temperature change value 232, the method proceeds to 314. Otherwise, at 316, the method generates and outputs the one or more notifications 240 to notify the operator that a leakage is detected in the first monitoring zone. For example, the method generates and outputs the one or more light control signals 242, the one or more audible control signals 244 and/or the operator interface data 246. The one or more light control signals 242 command the indicator light 49 associated with the first monitoring zone to illuminate, thereby notifying the operator of the leak. The one or more audible control signals 244 command the speaker 48 to output an audible message, such as "Warning—Leak Detected First Zone" and/or an audible tone. The operator interface data 246 includes data for rendering one or more graphical and/or textual messages on the display 46 that indicate that a leak has been detected in the first monitoring zone.

At 314, the method receives and processes the sensor signals from the sensor 104 of the second monitoring zone to determine the current temperature of the second monitoring zone. At 318, the method retrieves the initial zone temperature value 214 for the second monitoring zone and compares the initial zone temperature value 214 for the second monitoring zone to the current temperature of the second monitoring zone. The method determines or computes the second zone change in temperature 226, in one example, by subtracting the initial zone temperature value 214 for the second monitoring zone from the current temperature of the second monitoring zone to determine the second zone change in temperature 226.

At 320, the method retrieves the threshold temperature change value 232 from the values datastore 208 and compares the second zone change in temperature 226 to the threshold temperature change value 232. If the second zone change in temperature 226 is less than the threshold temperature change value 232, the method proceeds to 322. Otherwise, at 324, the method generates and outputs the one or more notifications 240 to notify the operator that a leakage is detected in the second monitoring zone. For example, the method generates and outputs the one or more light control signals 242, the one or more audible control signals 244 and/or the operator interface data 246. The one or more light control signals 242 command the indicator light 49 associated with the second monitoring zone to illuminate, thereby notifying the operator of the leak. The one or more audible control signals 244 command the speaker 48 to output an audible message, such as "Warning—Leak Detected Second Zone" and/or an audible tone. The operator interface data 246 includes data for rendering one or more graphical and/or textual messages on the display 46 that indicate that a leak has been detected in the second monitoring zone.

At 322, the method receives and processes the sensor signals from the sensor 104 of the third monitoring zone to determine the current temperature of the third monitoring zone. At 326, the method retrieves the initial zone temperature value 214 for the third monitoring zone and compares the initial zone temperature value 214 for the third monitoring zone to the current temperature of the third monitoring zone. The method determines or computes the third zone change in temperature 228, in one example, by subtracting the initial zone temperature value 214 for the third monitoring zone from the current temperature of the third monitoring zone to determine the third zone change in temperature 228.

At 328, the method retrieves the threshold temperature change value 232 from the values datastore 208 and compares the third zone change in temperature 228 to the threshold temperature change value 232. If the third zone change in temperature 228 is less than the threshold temperature change value 232, the method ends at 330. Otherwise, at 332, the method generates and outputs the one or more notifications 240 to notify the operator that a leakage is detected in the third monitoring zone. For example, the method generates and outputs the one or more light control signals 242, the one or more audible control signals 244 and/or the operator interface data 246. The one or more light control signals 242 command the indicator light 49 associated with the third monitoring zone to illuminate, thereby notifying the operator of the leak. The one or more audible control signals 244 command the speaker 48 to output an audible message, such as "Warning—Leak Detected Third Zone" and/or an audible tone. The operator interface data 246 includes data for rendering one or more graphical and/or textual messages on the display 46 that indicate that a leak has been detected in the third monitoring zone.

It should be noted that while the nutrient applicator 12 has been described and illustrated herein for being used with the nutrient leakage detection system 100, the nutrient leakage detection system 100 may be used with various types of nutrient applicators 12. In other embodiments, the nutrient leakage detection system 100 may be coupled to a nutrient applicator that follows a field planter or seeder or no-till air drill (not shown) that puts seeds into selected positions in rows of soil and covers the seeds with soil. In this configuration, the subsequent nutrient applicator releases or sprays compounds near the seeds in a region adjacent to where the seeds are planted. Alternatively, for some compounds, the nutrient applicator may also precede a field planter. In this example, the nutrient applicator first injects the compound into the soil, which is then followed by seed planting. For example, in a no-till planter application, a compound of starter fertilizer and anhydrous ammonia are mixed together and put into tanks on the field planter and optionally also on a trailer towed behind the field planter. Through a coulter or disk having an associated nutrient dispenser, the compound is injected and placed near the seed (e.g. about 1-3 inches away from the seed). In these embodiments with field planters, both the fertilizer and seeds are effectively placed into the soil during one drive pass through the field. In any of these embodiments, the nutrient leakage detection system 100 may be employed.

As will be appreciated by one skilled in the art, certain aspects of the disclosed subject matter can be embodied as a method, system (e.g., a work vehicle control system included in a work vehicle), or computer program product. Accordingly, certain embodiments can be implemented entirely as hardware, entirely as software (including firmware, resident software, micro-code, etc.) or as a combination of software and hardware (and other) aspects. Furthermore, certain embodiments can take the form of a computer program product on a computer-usable storage medium having computer-usable program code embodied in the medium.

Any suitable computer usable or computer readable medium can be utilized. The computer usable medium can be a computer readable signal medium or a computer readable storage medium. A computer-usable, or computer-readable, storage medium (including a storage device associated with a computing device or client electronic device) can be, for example, but is not limited to, an electronic, magnetic, optical, electromagnetic, infrared, or semiconductor system, apparatus, or device, or any suitable combination of the foregoing. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device. In the context of this document, a computer-usable, or computer-readable, storage medium can be any tangible medium that can contain, or store a program for use by or in connection with the instruction execution system, apparatus, or device.

A computer readable signal medium can include a propagated data signal with computer readable program code embodied therein, for example, in baseband or as part of a carrier wave. Such a propagated signal can take any of a variety of forms, including, but not limited to, electromagnetic, optical, or any suitable combination thereof. A computer readable signal medium can be non-transitory and can be any computer readable medium that is not a computer readable storage medium and that can communicate, propagate, or transport a program for use by or in connection with an instruction execution system, apparatus, or device.

Aspects of certain embodiments are described herein can be described with reference to flowchart illustrations and/or block diagrams of methods, apparatus (systems) and computer program products according to embodiments of the disclosure. It will be understood that each block of any such flowchart illustrations and/or block diagrams, and combinations of blocks in such flowchart illustrations and/or block diagrams, can be implemented by computer program instructions. These computer program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions can also be stored in a computer-readable memory that can direct a computer or other programmable data processing apparatus to function in a particular manner, such that the instructions stored in the computer-readable memory produce an article of manufacture including instructions which implement the function/act specified in the flowchart and/or block diagram block or blocks.

The computer program instructions can also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

Any flowchart and block diagrams in the figures, or similar discussion above, can illustrate the architecture, functionality, and operation of possible implementations of systems, methods and computer program products according to various embodiments of the present disclosure. In this regard, each block in the flowchart or block diagrams can represent a module, segment, or portion of code, which includes one or more executable instructions for implementing the specified logical function(s). It should also be noted that, in some alternative implementations, the functions noted in the block (or otherwise described herein) can occur out of the order noted in the figures. For example, two blocks shown in succession (or two operations described in succession) can, in fact, be executed substantially concurrently, or the blocks (or operations) can sometimes be executed in the reverse order, depending upon the functionality involved. It will also be noted that each block of any block diagram and/or flowchart illustration, and combinations of blocks in any block diagrams and/or flowchart illustrations, can be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. Explicitly referenced embodiments herein were chosen and described in order to best explain the principles of the disclosure and their practical application, and to enable others of ordinary skill in the art to understand the disclosure and recognize many alternatives, modifications, and variations on the described example(s). Accordingly, various embodiments and implementations other than those explicitly described are within the scope of the following claims.

What is claimed is:

1. A method for detecting a leakage of a nutrient from soil, the nutrient applied by a nutrient applicator associated with a work vehicle, the method comprising:
   receiving, by one or more processors, sensor signals from at least one sensor coupled to a nutrient applicator that observes a temperature of the soil within each of a plurality of monitoring zones and generates sensor signals based on the observation;
   processing, by the one or more processors, the sensor signals to determine a temperature of the soil at each monitoring zone of the plurality of monitoring zones;
   determining, by the one or more processors, whether the observed temperature of the soil at each monitoring zone of the plurality of monitoring zones exceeds a pre-defined threshold temperature; and
   generating, by the one or more processors, one or more notifications to a human-machine interface that the nutrient has leaked from the soil based on the observed temperature of the soil exceeding the pre-defined threshold temperature and which monitoring zone of the plurality of monitoring zones the observed temperature of the soil exceeds the pre-defined threshold.

2. The method of claim 1, wherein the at least one sensor comprises a plurality of sensors, each of the plurality of sensors is coupled to the nutrient applicator to define the plurality of monitoring zones, and the method further comprises:
   receiving, by the one or more processors, sensor signals from each of the plurality of sensors;
   processing, by the one or more processors, the sensor signals from each of the plurality of sensors to determine a change in temperature of the soil at each monitoring zone of the plurality of monitoring zones;
   determining, by the one or more processors, for each monitoring zone of the plurality of monitoring zones whether the change in temperature of the soil at the respective monitoring zone exceeds the pre-defined threshold; and
   generating, by the one or more processors, the one or more notifications to the human-machine interface of the work vehicle that the nutrient has leaked from the soil based on the change in temperature of the soil exceeding the pre-defined threshold for one of the plurality of monitoring zones.

3. The method of claim 2, wherein generating, by the one or more processors, the one or more notifications further comprises generating, by the one or more processors, the one or more notifications that indicate which monitoring zone of the plurality of monitoring zones the change in temperature of the soil exceeds the pre-defined threshold.

4. The method of claim 1, wherein generating, by the one or more processors, the one or more notifications further comprises at least one of generating, by the one or more processors, operator interface data for rendering a warning message on a display associated with the work vehicle, generating, by the one or more processors, one or more control signals for an audible device to provide an audible notification to the operator and generating, by the one or more processors, one or more control signals for an indicator light to provide a visual notification to the operator.

5. The method of claim 1, further comprising:
   receiving, by the one or more processors, input to enable the detection of the leakage of the nutrient from the soil from a source associated with the work vehicle;
   receiving, by the one or more processors, the sensor signals from at least one sensor coupled to the nutrient applicator;
   processing, by the one or more processors, the sensor signals to determine an initial temperature of the soil; and
   storing, by the one or more processors, the initial temperature in a datastore.

6. The method of claim 5, wherein determining whether the observed temperature of the soil exceeds the pre-defined threshold further comprises:
   retrieving, by the one or more processors, the initial temperature of the soil from the datastore;
   processing, by the one or more processors, the sensor signals to determine a current temperature of the soil;
   comparing, by the one or more processors, the initial temperature to the current temperature of the soil to determine a change in temperature of the soil; and
   determining, by the one or more processors, whether the change in temperature of the soil exceeds a pre-defined threshold for the change in temperature.

7. A system for detecting a leakage of a nutrient from soil, the nutrient applied by a nutrient applicator associated with a work vehicle, the system comprising:
   at least one sensor coupled to a nutrient applicator that observes a temperature of the soil within each of a plurality of zones and generates sensor signals based on the observation; and
   a controller, having one or more processors, that:
      process the sensor signals to determine a change in temperature of the soil at each monitoring zone of the plurality of zones;
      determine whether the change in temperature of the soil at each zone of the plurality of zones exceeds a pre-defined threshold for the change in temperature; and
      generate one or more notifications to an operator of the work vehicle that the nutrient has leaked from the soil based on the change in temperature of the soil exceeding the pre-defined threshold and which zone of the plurality of zones the change in temperature of the sol exceeds the pre-defined threshold.

8. The system of claim 7, wherein the at least one sensor is coupled to the nutrient applicator so as to be a distance above the soil.

9. The system of claim 7, wherein the at least one sensor is coupled to the nutrient applicator so as to be substantially perpendicular to the soil.

10. The system of claim 7, wherein the at least one sensor is a thermocouple coupled to a sensor mounting bracket, and the sensor mounting bracket couples the at least one sensor to the nutrient applicator so as to be positioned behind a soil closing tool of the nutrient applicator in a direction of travel of the work vehicle.

11. The system of claim 7, wherein the at least one sensor comprises a plurality of sensors, each of the plurality of sensors is coupled to a respective zone of the plurality of zones of the nutrient applicator, and the one or more processors:

receive sensor signals from each of the plurality of sensors;

process the sensor signals from each of the plurality of sensors to determine the change in temperature of the soil at each zone of the plurality of zones; and determine for each zone of the plurality of zones whether the change in temperature of the soil at the respective zone exceeds the pre-defined threshold.

12. The system of claim 7, wherein the one or more notifications further comprise at least one of operator interface data for rendering a warning message on a display associated with the work vehicle, one or more control signals for an audible device to provide an audible notification to the operator and one or more control signals for an indicator light to provide a visual notification to the operator.

13. The system of claim 7, wherein the one or more processors receive input to enable the detection of the leakage of the nutrient from the soil from a source associated with the work vehicle, receive the sensor signals from at least one sensor coupled to the nutrient applicator, process the sensor signals to determine an initial temperature of the soil and store the initial temperature in a datastore.

14. The system of claim 13, wherein the one or more processors retrieve the initial temperature of the soil from the datastore, process the sensor signals to determine a current temperature of the soil, compare the initial temperature to the current temperature of the soil and determine the change in temperature of the soil based on the comparison.

15. A system for detecting a leakage of a nutrient from soil, the nutrient applied by a nutrient applicator associated with a work vehicle, the system comprising:
  at least one sensor coupled to a nutrient applicator that observes a temperature of the soil within each of a plurality of zones and generates sensor signals based on the observation, the at least one sensor coupled to the nutrient applicator so as to be positioned behind the nutrient applicator in a direction of travel of the work vehicle; and
  a controller, having one or more processors, that:
    receive the sensor signals from at least one sensor coupled to the nutrient applicator;
    process the sensor signals to determine an initial temperature of the soil at each zone of the plurality of monitoring zones;
    receive the sensor signals from at least one sensor and process the sensor signals to determine a current temperature of the soil at each zone of the plurality of zones;
    compare the initial temperature to the current temperature of the soil to determine a change in temperature of the soil at each zone of the plurality zones;
    determine whether the change in temperature of the soil at each zone of the plurality of zones exceeds a pre-defined threshold for the change in temperature; and
    generate one or more notifications to an operator of the work vehicle that the nutrient has leaked from the soil based on the change in temperature of the soil exceeding the pre-defined threshold and which zone of the plurality of zones the change in temperature of the soil exceeds the pre-defined threshold.

16. The system of claim 15, wherein the at least one sensor is a thermocouple coupled to the nutrient applicator so as to be a distance above the soil and substantially perpendicular to the soil.

17. The system of claim 15, wherein the at least one sensor is coupled to a sensor mounting bracket, and the sensor mounting bracket couples the at least one sensor to the nutrient applicator so as to be positioned behind a closing tool of the nutrient applicator in a direction of travel of the work vehicle.

18. The system of claim 17, wherein the at least one sensor comprises a plurality of sensors, each of the plurality of sensors is coupled to a respective zone of the plurality of zones of the nutrient applicator, and the one or more processors:
  receive sensor signals from each of the plurality of sensors;
  process the sensor signals from each of the plurality of sensors to determine the change in temperature of the soil at each zone of the plurality of zones;
  determine for each zone of the plurality of zones whether the change in temperature of the soil at the respective zone exceeds the pre-defined threshold; and
  generate the one or more notifications to the operator of the work vehicle that the nutrient has leaked from the soil based on the change in temperature of the soil exceeding the pre-defined threshold for one of the plurality of zones.

* * * * *

UNITED STATES PATENT AND TRADEMARK OFFICE
CERTIFICATE OF CORRECTION

PATENT NO. : 10,255,770 B2
APPLICATION NO. : 15/596962
DATED : April 9, 2019
INVENTOR(S) : Barker Page 1 of 1

It is certified that error appears in the above-identified patent and that said Letters Patent is hereby corrected as shown below:

In the Claims

In Column 18, Claim 7, Line 50, delete "sol" and insert -- soil --, therefor.

In Column 20, Claim 15, Line 7, delete "plurality zones;" and insert -- plurality of zones; --, therefor.

Signed and Sealed this
Thirteenth Day of August, 2019

Andrei Iancu
*Director of the United States Patent and Trademark Office*